United States Patent
Pires et al.

(10) Patent No.: US 9,936,790 B2
(45) Date of Patent: Apr. 10, 2018

(54) COSMETIC APPLICATOR

(71) Applicant: ZEN DESIGN SOLUTIONS LIMITED, Kowloon (HK)

(72) Inventors: Leo Clifford Pires, Basking Ridge, NJ (US); Smita Srivastava, New Delhi (IN); Iti Seth, Faridabad (IN); Rahul Bose, New Delhi (IN)

(73) Assignee: ZEN DESIGN SOLUTIONS LIMITED, Kowloon, Hong Kong (CN)

( * ) Notice: Subject to any disclaimer, the term of this patent is extended or adjusted under 35 U.S.C. 154(b) by 0 days.

(21) Appl. No.: 15/364,187

(22) Filed: Nov. 29, 2016

(65) Prior Publication Data
US 2017/0071315 A1    Mar. 16, 2017

Related U.S. Application Data

(63) Continuation-in-part of application No. 14/700,884, filed on Apr. 30, 2015.

(51) Int. Cl.
| | |
|---|---|
| *A45D 34/04* | (2006.01) |
| *A45D 40/26* | (2006.01) |
| *A61M 35/00* | (2006.01) |
| *A45D 29/00* | (2006.01) |
| *A61F 7/00* | (2006.01) |

(52) U.S. Cl.
CPC ............. *A45D 34/04* (2013.01); *A45D 29/00* (2013.01); *A45D 34/045* (2013.01); *A45D 40/26* (2013.01); *A45D 40/265* (2013.01); *A61M 35/003* (2013.01); *A45D 2200/1009* (2013.01); *A45D 2200/15* (2013.01); *A61F 7/00* (2013.01); *A61F 2007/0052* (2013.01); *A61M 2210/04* (2013.01)

(58) Field of Classification Search
CPC ............................ A45D 34/045; A45D 40/265
USPC .................. 401/126, 127, 128, 129, 130
See application file for complete search history.

(56) References Cited

U.S. PATENT DOCUMENTS

| | | |
|---|---|---|
| 1,999,642 A | 4/1935 | Shepherd |
| 6,033,143 A | 3/2000 | Gueret |
| 6,655,390 B2 | 12/2003 | Gueret |
| 2008/0038043 A1 | 2/2008 | Tranchant |

*Primary Examiner* — David Walczak
*Assistant Examiner* — Joshua Wiljanen
(74) *Attorney, Agent, or Firm* — Patterson + Sheridan, LLP

(57) ABSTRACT

An applicator comprising at least two applicator elements and one of the at least two applicator elements at least partially surrounds or encompasses other of the at least two applicator elements. One of the at least two applicator element is constructed from a filament constructed at least partially from a thermal storage material that is capable of retaining heat or cold for application to a body, and comprises at least two loops which provide a discontinuous application surface.

20 Claims, 11 Drawing Sheets

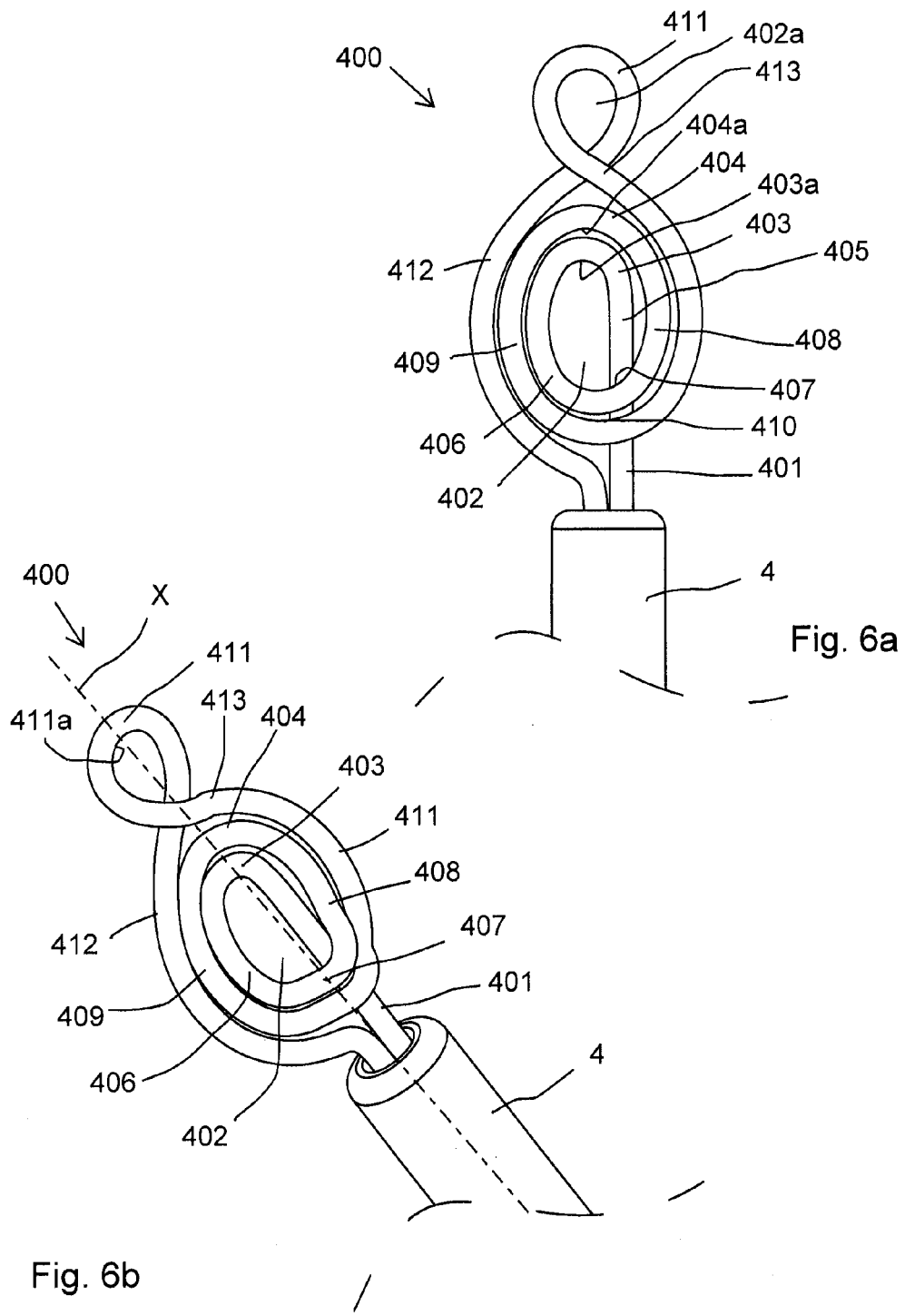

COSMETIC APPLICATOR

CROSS-REFERENCE TO RELATED APPLICATION

This patent application is a continuation in part of and claims the benefit of priority to U.S. patent application Ser. No. 14/700,884 filed on Apr. 30, 2015, which in turn claims the benefit of priority to Indian Provisional Application Ser. No. 1263/DEL/2014, filed on May 9, 2014. The disclosure of each of the aforementioned patent applications is incorporated by reference herein in its entirety for any purpose whatsoever.

BACKGROUND

Field of the Invention

Embodiments of the present disclosure generally relate to an applicator comprising a stem having a handle at its proximal end and an applicator element at its distal end. The applicator element is constructed, at least partially, from a thermal storage material that is capable of retaining heat or cold for application to a body. The applicator may be used to apply a cosmetic product, medicinal product, or a personal care product.

Description of the Related Art

The present disclosure relates to a packaging and applicator device for products including cosmetic product, medicinal product, personal care product, or other types of product.

U.S. Pat. No. 6,655,390 discloses an applicator for applying a composition on eyelashes or eyebrows. The applicator comprises branches that are united at ends thereof and that carry protruding elements that might be flocked. At least a fraction of the protruding elements can be made on each opposite region of a support by being molded or injected onto the support, or by being cut out and deformed from a sheet of metal.

U.S. Pat. No. 6,033,143 discloses an applicator including a cord in the form of a loop, provided with a flock coating. This cord includes, for example, a core made of polyvinyl chloride elastomer, polyurethane elastomer or polyester elastomer, this core having a diameter of 0.1 to 3 mm.

U.S. Pat. No. 1,999,642 discloses an applicator having a stem and a tip in the form of a loop adapted to hold a quantity of liquid and bent laterally with respect to the stem to facilitate bringing the loop into substantially flat contact with the surface being treated. The tip may be flattened to improve the contact between it and the surface being treated and to facilitate the transfer of liquid there from to said surface.

U.S. Patent Application No. 2008038043 discloses an applicator having a stem and a tip in the form of a loop having a smooth surface. The loop is made of a flexible material presenting a modulus of elasticity less than or equal to 300 megapascals (MPa) at 20[deg.] C.

The existing applicators are typically designed to achieve a particular effect. None of the applicators described above provide any type of treatment, therapy, or sensation for example a cooling or heating sensation to the surface being treated. Therefore it is an object of the present disclosure to provide an applicator capable of providing cooling or heating sensation on skin.

It is also an object of the present disclosure to provide an applicator which is capable of providing a larger contact area on the surface being treated.

It is further an object of the present disclosure to provide an applicator having a cavity/reservoir for being loaded with product, the cavity may constitute a supply of product, thereby enabling the applicator to be used for a greater length of time or enabling a greater quantity of product to be deposited more easily.

SUMMARY

The present disclosure generally relates to an applicator for applying a product to a surface such as a face, head, skin, hair or body of a person, to achieve one or more effects and to impart a treatment, therapy, and/or sensation (e.g., a cooling or warming treatment, therapy, or sensation) during use. The product may be a cosmetic product, medicinal product, personal care product, or other types of product. The cosmetic product may include, but are not limited to, skin treatment, mascara, lash growth, lash treatment, conditioner, primer, colorant, brow treatment, nail treatment, lip gloss, lipstick, eye shadow, and the like. The cosmetic product may be in the form of, for example, liquids, gels, creams, oil-based products, wax-based products, water-based products, or the like.

According to an embodiment, the applicator comprises a stem having a handle at its proximal end and an applicator element at its distal end.

According to another embodiment, the applicator element is constructed, at least partially, from a thermal storage material that is capable of retaining heat or cold for application to a body. The thermal storage material may comprise, for example, a metal, ceramic, glass, and/or other material with a relatively high thermal storage capacity and/or thermal conductivity. When used to apply the product to the body, the thermal storage material of the applicator element may impart a cooling or warming treatment, therapy, or sensation to the body, thereby accentuating the application of the product.

According to another embodiment, there is provided a packaging and applicator device comprising a receptacle that may contain the product to be applied and the applicator. The applicator of the present disclosure is housed in the receptacle and the handle of the applicator may also constitute a closure cap that seals the receptacle when closed.

According to another embodiment, the stem has a longitudinal axis, which may be rectilinear but in other embodiments, the stem may be curved, may be bendable, may have an elbow, etc. The handle and the stem may be constructed of plastic (e.g., polypropylene (PP), acrylonitrile butadiene styrene (ABS), Polyoxymethylene (POM)), or any other suitable material.

According to another embodiment, the applicator element comprises at least one filament having at least one end attached to the distal end of the stem. According to an alternate embodiment the at least one filament has at least one other end also fixed to the distal end of the stem. However, it would not be beyond the scope of the present disclosure if the at least one other end of the at least one filament of the applicator element is free and is not attached to the distal end of the stem.

According to another embodiment, the at least one filament comprises of one or more materials. The at least one filament may comprise a continuous single length of one material or it may comprise of two or more portions of one or more materials connected together. The two or more portions may be connected together or formed as one by various attachment means like adhesive, snap fitting, integrally molded, press molding, bi-injection molding and the like.

At least one portion of the at least one filament is constructed of a material capable of holding and retaining a thermal charge. In other embodiments, the at least one filament is constructed of any suitable material capable of retaining and/or transferring heat or cold during application of the product. For example, the material may include, but is not limited to, metal, glass, and/or ceramics. The metal may include carbon, steel, stainless steel, aluminum, brass, chrome, copper, gold, nickel, platinum, silver, titanium, alloys, combinations thereof, or the like. Further, the material may include a base metal of zinc and alloying elements of aluminum, magnesium, and copper (e.g., Zamac).

In other embodiments, stones, additives, resin, magnetic components, or any other components may be added separately or in combination to the metal, ceramic, and/or glass. For instance, stones may include but are not limited to, jade, opal, turquoise, amethyst, aquamarine, Tiger's eye, coral, amber, quartz, onyx, and tanzanite. In other embodiments, magnetic components may be added that include but are not limited to, magnetic powders, magnetic compounds, or magnetic strips. The magnetic powders may include but are not limited to, ferrite magnetic powder, barium ferrite magnetic powder, strontium ferrite magnetic powder, rare earth magnetic powder, iron oxide compound, a combination of aluminium (aluminum), nickel, and cobalt (Alnico) with iron and small amounts of other components.

According to another embodiment, the at least one filament is bent to provide a discontinuous application surface by forming at least one cavity/reservoir. Alternatively, different portions of one or more material may be connected or integrally molded together to provide a discontinuous application surface by forming at least one cavity/reservoir. The two or more portions may be connected together or formed as one by various attachment means like adhesive, snap fitting, integrally molded, press molding and the like.

The cavity/reservoir is made so as to be suitable for being loaded with the product. The cavity/reservoir may constitute a supply of product, thereby enabling the applicator element to be used for a greater length of time or enabling a greater quantity of product to be deposited more easily, for example, to reinforce a makeup effect, such as glossiness of a gloss.

According to another embodiment, the cavity/reservoir opens to the outside. The cavity/reservoir which opens to the outside further provides air cooling of the product as when the applicator element loaded with the product is removed from the receptacle, the product stored in the cavity is exposed to the air from both the sides of the applicator element.

According to another embodiment, the applicator element comprises at least two loops forming one or more cavities or reservoirs for holding the product.

As used herein, the term "loop" includes a substantially U-shaped curve or U-shaped bend. The "loop" within the present disclosure encompasses both open ended loops and close ended loops.

According to still another embodiment, the applicator element comprises at least two loops wherein each of the at least two loops is formed by giving a reverse bend to at least one portion of the at least one filament, in a direction towards the distal end of the stem. The at least two loops extend in a direction of the applicator.

According to another embodiment, the at least two loops of the applicator element may be formed by injection molding, bi-injection molding, multi-injection molding, press molding and the like.

According to another embodiment, a concave side of the reverse bend of the each of the at least two loops faces towards the distal end of the stem.

According to another embodiment, each of the at least two loops has a pair of legs.

According to another embodiment, at least one leg from a pair of legs of each of the at least two loops, is not parallel to the longitudinal axis of the stem.

According to another embodiment, the legs of each of the at least two loops lie on opposite sides of the longitudinal axis of the stem of the applicator.

According to another alternate embodiment, the legs of each of the at least two loops lie on same side of the longitudinal axis of the stem of the applicator.

According to another embodiment, the at least two loops may lie in same plane or in different planes.

According to another embodiment, at least two portions of each of the at least two loops may lie in same plane or in different planes.

According to first exemplary embodiment, the applicator element comprises a first loop and a second loop forming a first cavity and a second cavity respectively.

According to the embodiment, the applicator element comprises an outer first loop forming a first cavity and an inner second loop forming a second cavity.

The at least one portion of the at least one filament whose one end is attached to the distal end of the stem is bent to provide a first loop or curve by giving the at least one portion of the at least one filament, a first reverse bend in a direction towards the distal end of the stem such that a concave side of the reverse bend/first curve faces towards the distal end of the stem. Further, at least one other portion of the at least one filament is bent again to provide a second loop or curve by giving the at least one other portion of the at least one filament, a second reverse bend in a direction towards the distal end of the stem such that a concave side of the second reverse bend faces towards the distal end of the stem.

According to the present embodiment, at least a portion of the first loop and at least a portion of the second loop may lie in the same plane or in different planes.

According to the present embodiment, at least one of the first loop and the second loop does not lie in a single plane.

According to an alternate embodiment, at least one of the first loop and the second loop lies in a single plane.

According to present embodiment, the first loop includes a pair of legs and the second loop includes another pair of legs.

According to present embodiment, each of the pair of legs of the first loop and the second loop lie on opposite sides of the longitudinal axis of the stem.

According to an embodiment, an end portion of one of the legs of the first loop is in continuum with starting portion of one of the legs of the second loop.

According to an embodiment, a third loop may be defined by the legs of the first and second loops, which are in continuum.

According to an embodiment, each leg from the pair of legs of the first loop may include a longitudinal axis that extends substantially parallel to a common plane. According to an alternate embodiment, the pair of legs of the first loop may include longitudinal axes that are not parallel to a common plane.

According to an embodiment, each leg from the pair of legs of the second loop may include a longitudinal axis that extends substantially parallel to a common plane. According to an alternate embodiment, the pair of legs of the second loop may include longitudinal axes that are not parallel to a common plane.

According to an alternate embodiment, one leg from the pair of legs of each of the first loop and the second loop lies forward of other leg from the pair of legs of said loop. The leg which lies forward of other leg is referred to as the upper leg and the leg which lies backward is referred to as the under leg.

According to the present embodiment, a pair of legs of at least one loop crosses one another at a point but may or may not touch each other at the point of crossing. The point of crossing may lie in a gap between the upper leg and the under leg.

According to a second exemplary embodiment, the applicator element comprises at least one filament which is bent to provide a discontinuous application surface by forming two adjacent loops forming two or more cavities.

According to the present embodiment, at least one portion of the at least one filament is bent to form a first loop by giving the at least one portion of the filament a first reverse bend in a direction towards the distal end of the stem, such that one leg of the first loop is longer than its other leg. A concave side of the first reverse bend faces towards the distal end of the stem. Further, at least one other portion of the at least one filament is bent again to provide a second loop by giving the at least one other portion of the filament, a second reverse bend in a direction towards the distal end of the stem, such that the first loop and the second loop are adjacent to each other and one leg of the adjacent second loop is longer than its other leg. A concave side of the second reverse bend faces towards the distal end of the stem.

According to present embodiment, adjacent first and second loops contact each other at two different points.

According to a third exemplary embodiment, the applicator element comprises at least one filament which is bent to provide a discontinuous application surface by forming at least two adjacent loops forming one or more cavities or reservoirs.

According to the present embodiment, at least one portion of the at least one filament is bent to provide a first loop by giving the at least one portion of the filament a first reverse bend in a direction towards the distal end of the stem, such that one leg of the first loop is longer than the other leg. A concave side of the first reverse bend faces the distal end of the stem. Further, the smaller leg of the first loop is curved such that it is substantially parallel to the longer leg of the first loop. Further, at least one other portion of the at least one filament is bent again to provide a second loop or curve by giving the at least one other portion of the filament a second reverse bend in a direction towards the distal end of the stem, such that one leg of the second loop is longer than its other leg. A concave side of the second reverse bend faces the distal end of the stem. Further, the smaller leg of the second loop is curved such that it is substantially parallel to its longer leg. The first loop and the second loop together form a first cavity or reservoir for holding the product.

Further, according to the present embodiment, the smaller legs of the pair of legs of the first loop and the second loop are in continuum and together form a third loop which further forms a second cavity/reservoir for holding the product.

According to the present embodiment the first loop and second loop are separated by third loop such that the first, second and third loops lie in the same plane.

According to an alternate embodiment, at least one of the first loop, the second loop or third loop does not lie in a single plane.

According to a fourth exemplary embodiment the applicator element comprises at least one filament bent to provide a discontinuous application surface by forming at least one cavity/reservoir.

According to present embodiment, the at least one filament is bent to provide at least one cavity/reservoir for holding the product. The at least one cavity/reservoir is formed by two loops. At least a portion of the at least one filament is bent to provide a first loop by giving the at least one portion of the at least one filament a first reverse bend in a direction towards the distal end of the stem, such that the first loop has one leg longer than its another leg. A concave side of the first reverse bend faces towards the distal end of the stem. Further, at least one other portion of the at least one filament is bent again to provide a second loop by giving the at least one other portion of the at least one filament a second reverse bend in a direction towards the distal end of the stem, such that the second loop also has one leg longer than its another leg. A concave side of the second reverse bend faces towards the distal end of the stem.

According to the present embodiment, the legs of the first loop lie on opposite sides of the longitudinal axis of the stem and the legs of the second loop also lie on opposite sides of the longitudinal axis of the stem.

Further, according to the present embodiment, end portion of smaller leg of the first loop is in continuum with starting portion of smaller leg of the second loop.

According to the present embodiment, a third loop forming a cavity may be defined by the smaller leg of the first loop and the smaller leg of the second loop, which are in continuum. A concave side of the third loop faces away from the distal end of the stem.

According to the present embodiment, the first loop and the second loop lie in different planes. Further, according to the present embodiment at least a portion of the second loop lies forward of at least a portion of the first loop such that the first loop is referred as under loop and the second loop is referred as upper loop. The smaller leg of the first loop and the smaller leg of the second loop cross each other at a point such that the smaller leg of the first loop is the under leg and the smaller leg of the second loop is the upper leg.

According to a fifth exemplary embodiment, the applicator element comprises at least one filament bent to provide at least one cavity/reservoir for holding the product. The at least one cavity/reservoir is formed by a first loop. At least a portion of the at least one filament is bent to provide a first loop by giving the at least one portion of the at least one filament a first reverse bend in a direction towards the distal end of the stem, such that the first loop has a leg longer than its another leg. A concave side of the first reverse bend faces the distal end of the stem. The two legs of the first loop lie in different planes such that one of the two legs is upper leg and the other leg is under leg. Further, the two legs of the first loop cross each other at a point. Further, at least one other portion of the at least one filament is bent again to provide a second loop or curve by giving the at least one other portion of the filament a second reverse bend in a direction towards the distal end of the stem, such that the first loop and the second loop are in close contact or substantially contiguous with each other. A concave side of the second reverse bend faces the distal end of the stem.

Further, the second loop has one leg smaller in length to another leg and lie in same plane. One of the legs of second loop meets one of the legs of the first loop at a point. Further, at least one other portion of the at least one filament is bent again to provide a third loop by giving the at least one portion of the filament a third reverse bend in a direction towards the distal end of the stem such that the third loop has two legs and at least one portion of each of the two legs lie on one side of the longitudinal axis of the stem and at least one other portion of each of the two legs lie on opposite side of the longitudinal axis of the stem. In other words, at least one other portion of the at least one filament is bent to provide a third loop or curve by bending the at least one other portion in form of "S" before giving a reverse bend in a direction towards the distal end of the stem. Further, third loop has an under leg and an upper leg crossing each other at point. The third loop forms a second cavity. Alternatively, the loops of the applicator element may be formed by injection molding, bi-injection molding, multi-injection molding, press molding and the like.

According to the present embodiment, the first loop, the second loop and the third loop lie in different planes.

According to the present embodiment, the first loop, the second loop and the third loop are in continuum.

In alternate embodiments of the present disclosure, a portion of the applicator element may be flocked.

In yet other alternate embodiments of the present disclosure, at least a portion of the applicator element may have texture.

According to an alternate embodiment of the present disclosure, the applicator may comprise at least two applicator elements and wherein one applicator element of the at least two applicator elements at least partially surrounds or encompasses the other applicator element. At least one applicator element of the at least two applicator elements is attached to a distal end of the stem. Further, at least one applicator element of the at least two applicator elements comprise at least one filament which is bent to provide a discontinuous application surface by forming at least one loop defining a cavity. According to another aspect, one applicator element of the at least two applicator elements may be made up of a material such as metal, plastic, silicone, sponge, foam, alloy, ceramic, stone, wood, rubber, sintered, porous material and/or combinations thereof or any other suitable material. Further, one of the at least two applicator elements may be flocked.

According to another alternate embodiment of the present disclosure, the applicator may be a flow through applicator and wherein one applicator element of the at least two applicator elements may include at least one dispensing orifice designed to dispense the product onto the application surface of said applicator element. Furthermore, the applicator may include a connecting collar for securely mounting the applicator to a cosmetic container having a receptacle for holding the product and wherein the product is dispensed from the container through said at least one orifice of the applicator element.

According to another alternate embodiment of the present disclosure, the applicator may be a flow through applicator and the product is dispensed from the container due to porosity of one applicator element of the at least two applicator elements.

According to another embodiment, the receptacle may be constructed of plastic (e.g., polypropylene (PP), acrylonitrile butadiene styrene (ABS), polyoxymethylene (POM)), or any other suitable material, for containing the products described below. The product in the receptacle may be cosmetic product, medicinal product, personal care product, or other types of product.

According to another embodiment, the receptacle has a substantially rectangular cross-sectional shape. According to alternate embodiments, the receptacle may have a substantial triangular cross-sectional shape, substantially circular cross-sectional shape (e.g., a cylindrical tube) or any other suitable receptacle shape.

According to another embodiment, the at least one filament may have a circular or a non-circular cross-section such as oval, elliptic, or polygonal cross-section.

According to another embodiment, a top of the receptacle may be provided with a neck in which a wiper member may be engaged. The wiper member is configured to remove any excess product from the stem and the applicator element when the applicator is removed from the receptacle to apply the product to the surface to be treated such as face, head, skin, lips, hair or body of a person. Preferably, the surface to be treated is skin of face.

According to another embodiment the handle may be screwed on the neck but in other embodiments, the handle may be fastened in some other way, for example, by snap-fastening.

The above and other objects, features and advantages of the present disclosure will become clear from the following description of the preferred embodiments when the same is read in conjunction with the accompanying drawings.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 6a and FIG. 6b illustrate a front view and a perspective view of an applicator according to fifth embodiment of the disclosure;

It is to be noted that the appended drawings illustrate only typical embodiments of this disclosure and are therefore not to be considered limiting of its scope, for the disclosure may admit to other equally effective embodiments.

DETAILED DESCRIPTION

Figure 1:
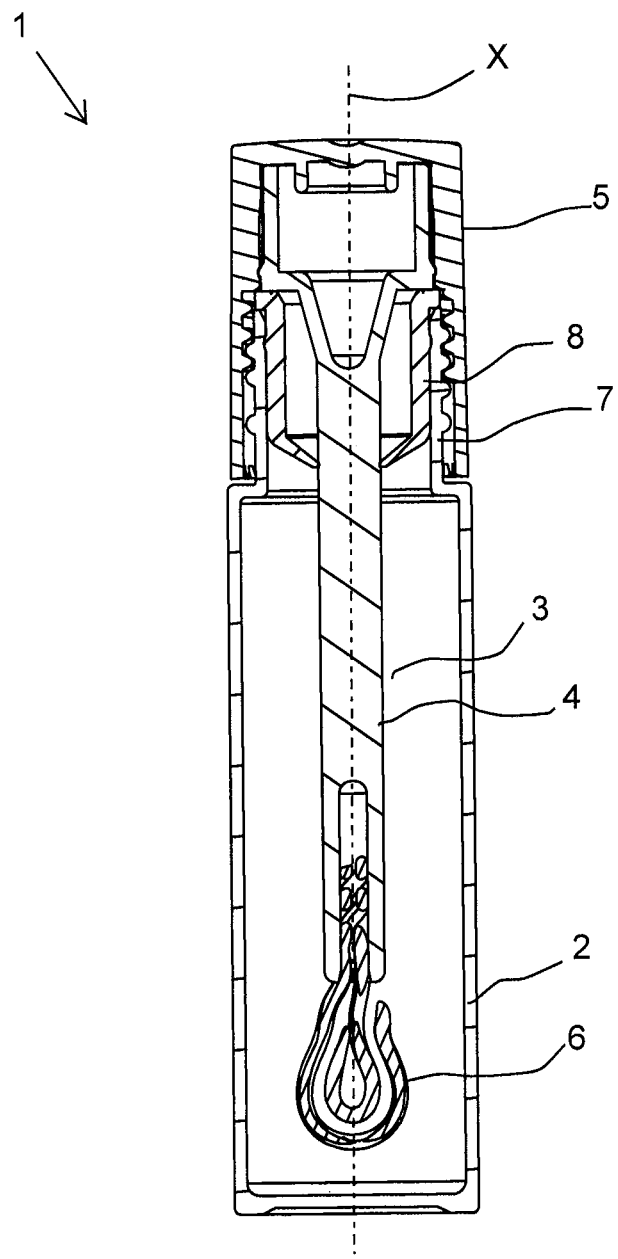
FIG. 1 illustrates a longitudinal sectional view of a packaging and applicator device according to first embodiment of the disclosure.

FIG. 1 shows a packaging and applicator device 1 comprising: a receptacle 2 that may contain a product (not shown) to be applied; and an applicator 3. The applicator 3 comprises a stem 4 elongated along a longitudinal axis X. The stem 4 is provided at its proximal end with a handle 5, which also constitutes a closure cap that seals the receptacle 2 when closed, and provided at a distal end thereof with an applicator element 6.

In the embodiment shown in FIG. 1, an axis X of the stem 4 is rectilinear, but in other embodiments, the stem 4 may be curved, may be bendable, may have an elbow, etc. The handle 5 and the stem 4 may be constructed of plastic (e.g., polypropylene (PP), acrylonitrile butadiene styrene (ABS), Polyoxymethylene (POM)), or any other suitable material.

The receptacle 2 may be constructed of plastic (e.g., polypropylene (PP), acrylonitrile butadiene styrene (ABS), polyoxymethylene (POM)), or any other suitable material, for containing the products described below.

The product in the receptacle 2 may be a cosmetic product, medicinal product, personal care product, or other types of product. The cosmetic product may include, but are not limited to, skin treatment, mascara, lash growth, lash treatment, conditioner, primer, colorant, brow treatment, nail treatment, lip gloss, lipstick, eye shadow and the like. The cosmetic product may be in the form of, for example, liquids, gels, creams, oil-based products, wax-based products, water-based products, or the like.

The receptacle 2 in the present embodiment has a substantially rectangular cross-sectional shape. However, a variety of receptacle cross-sectional shapes and types are contemplated. For example, the receptacle 2 may have a substantial triangular cross-sectional shape, substantially circular cross-sectional shape (e.g., a cylindrical tube) or any other suitable receptacle shape.

A top of the receptacle 2 is provided with a neck 7 in which a wiper member 8 is engaged. The wiper member 8 is configured to remove any excess product from the stem 4 and the applicator element 6 when the applicator 3 is removed from the receptacle 2 to apply the product to a surface such as a face, head, skin, hair or body of a person, to achieve one or more effects and to impart a treatment, therapy, and/or sensation (e.g., a cooling or warming treatment, therapy, or sensation) during use.

The wiper member 8 may be made of a material, for example, a polyolefin or an elastomer. The polyolefin may be polyethylene, for example, such as low- or high-density polyethylene.

The handle 5 is screwed on the neck 7, but in other embodiments, the handle 5 may be fastened in some other way, for example, by snap-fastening.

Figure 2A:
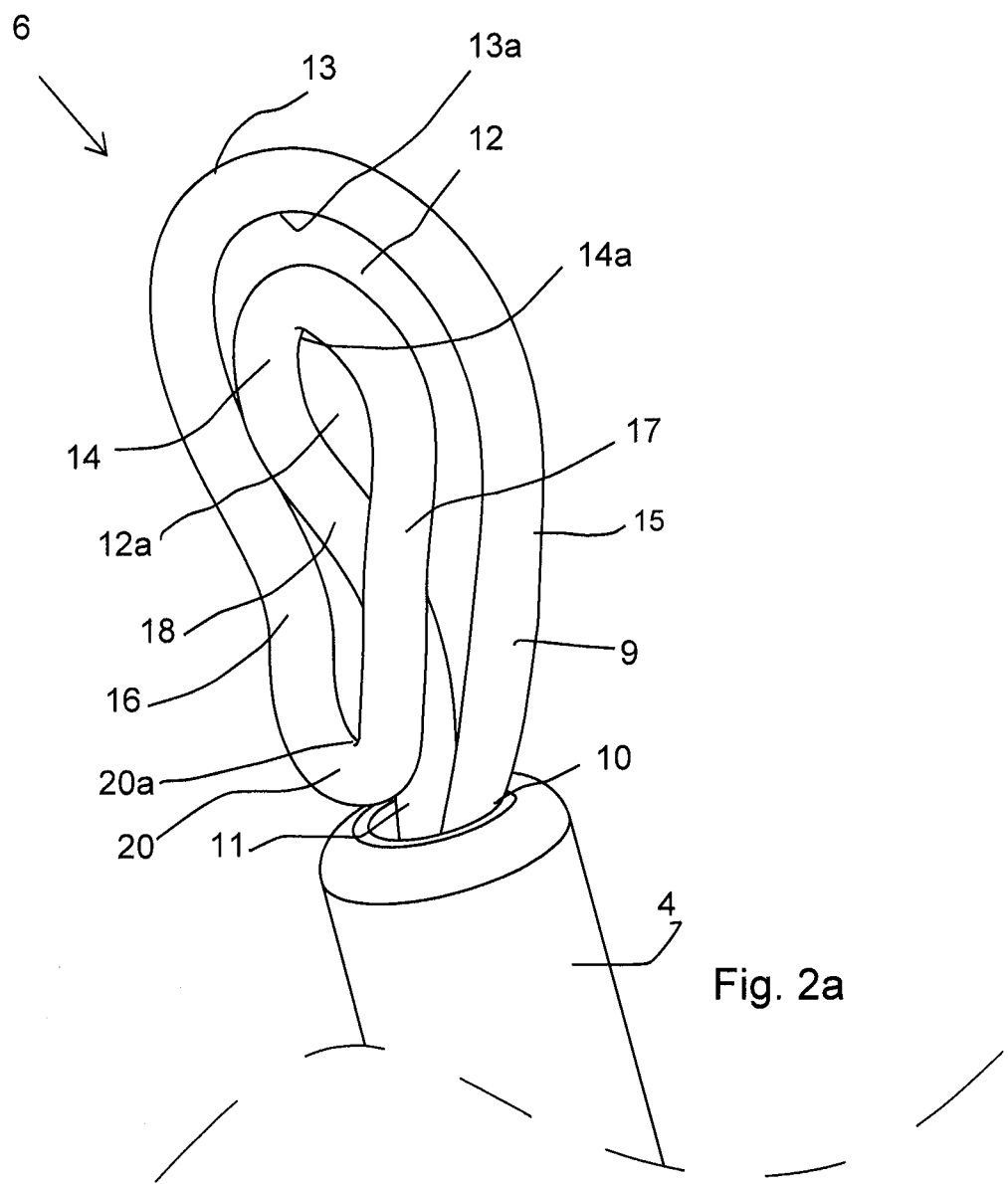
FIG. 2a and FIG. 2b illustrate a perspective view and a front view of an applicator of the packaging and applicator device of FIG. 1 according to first embodiment of the disclosure.
Figure 2B:
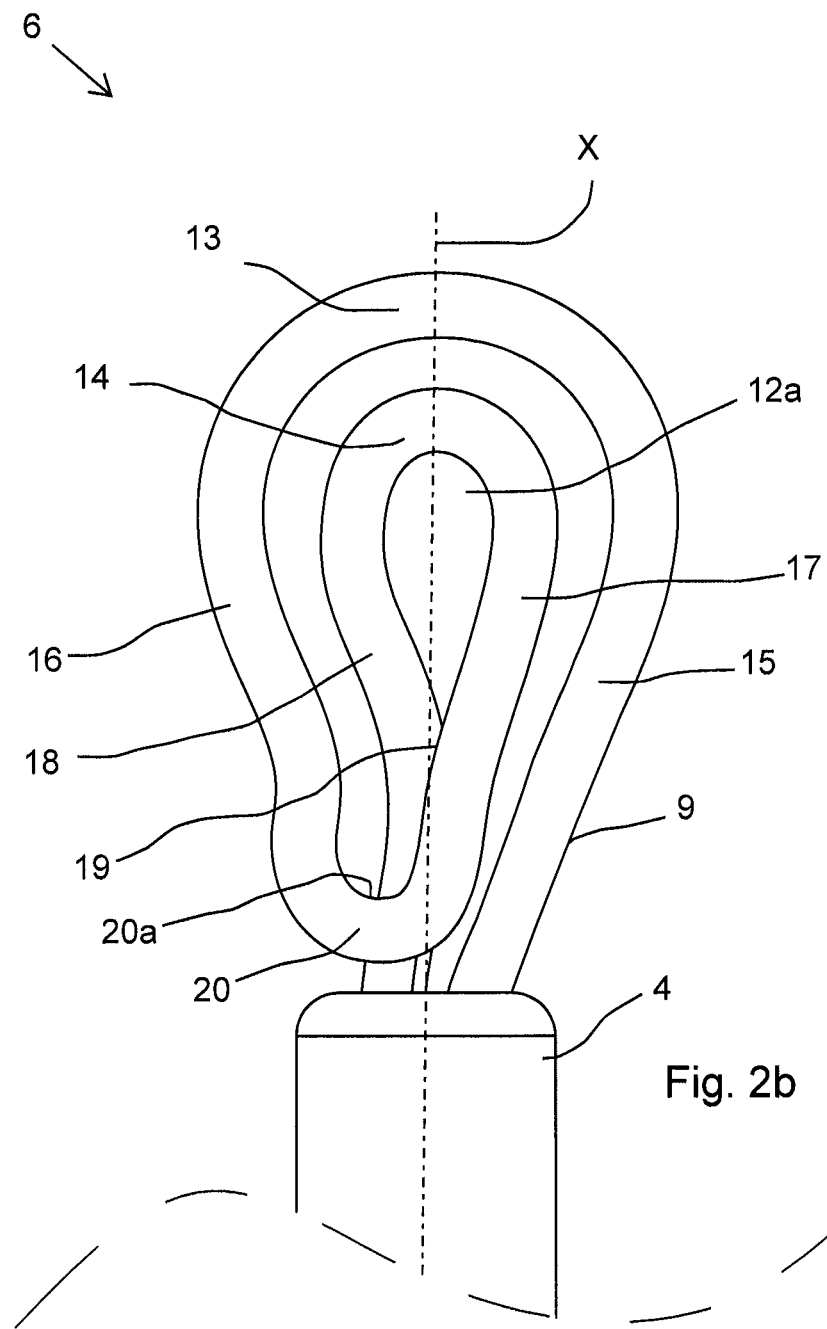
Figure 2C:
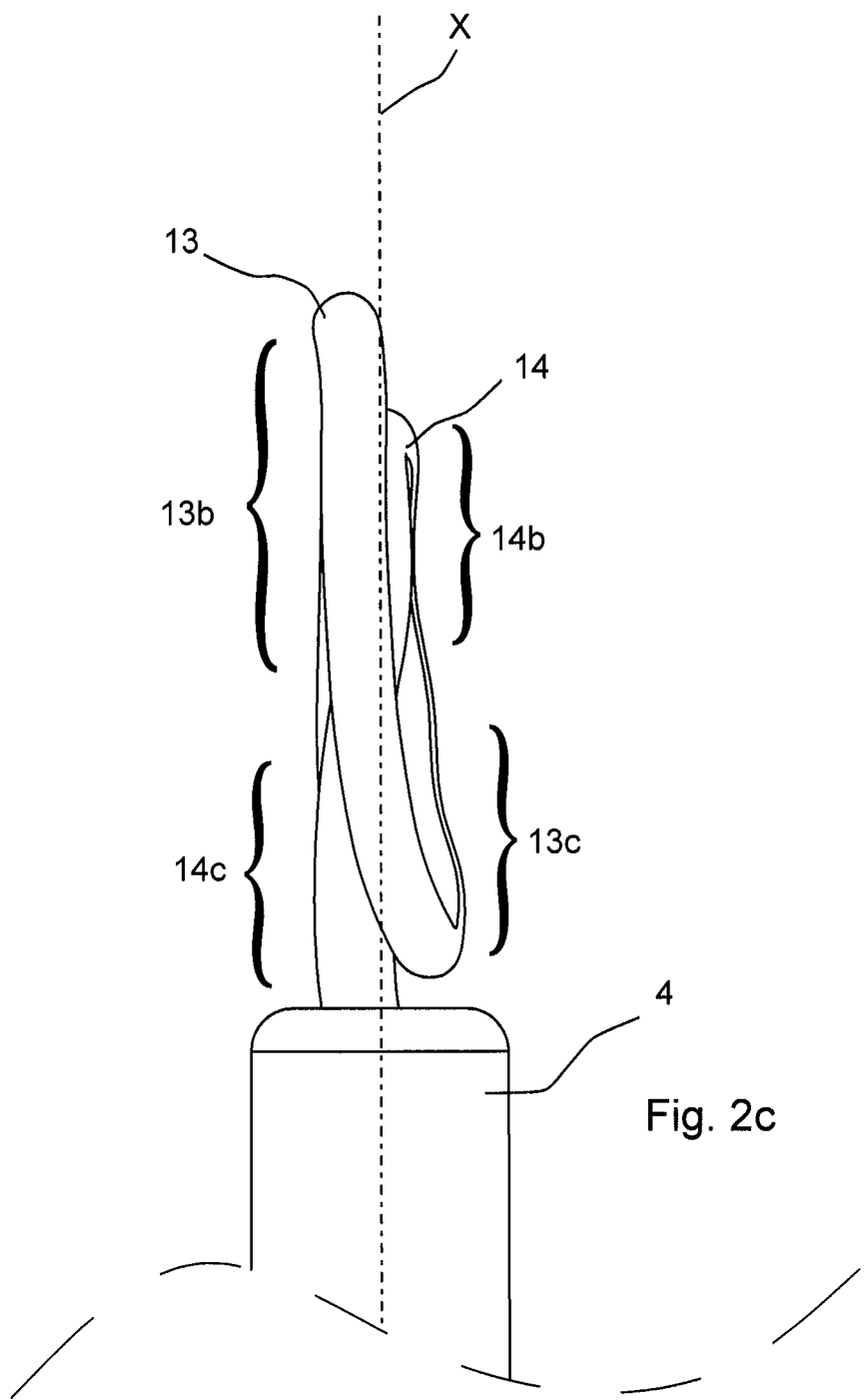
FIG. 2c illustrates a side view of the applicator of FIG. 2b.

FIGS. 2a, 2b and 2c show a perspective view, a front view and a side view respectively, of the applicator element 6 according to first embodiment of the disclosure.

As shown in FIGS. 2a and 2b, the applicator element 6 comprises at least one filament 9 having at least one end 10 attached to the distal end of the stem 4. The at least one filament 9 has at least one other end 11 also fixed to the distal end of the stem 4. However, it would not be beyond the scope of the present disclosure, if the at least one other end 11 is free and is not attached to the distal end of the stem 4.

The at least one filament 9 comprises a continuous single length of a material bent to provide a discontinuous application surface by forming at least one cavity/reservoir. It would not be beyond the scope of the present disclosure, if the at least one filament 9 of the applicator element 6 comprises of more than one material. The cavity/reservoir is made so as to be suitable for being loaded with the product. The cavity/reservoir may constitute a supply of product, thereby enabling the applicator element 6 to be used for a greater length of time or enabling a greater quantity of product to be deposited more easily, for example, to reinforce a makeup effect, such as glossiness of a gloss.

According to the present embodiment, the at least one filament 9 is bent to provide two cavities or reservoirs 12 and 12a for holding the product. Alternatively, the applicator element may be formed by injection molding, bi-injection molding, multi-injection molding, press molding and the like.

In the present embodiment, the applicator element 6 comprises a first loop 13 forming a first cavity 12 and a second loop 14 forming a second cavity 12a.

The first and the second cavities 12 and 12a open to the outside. It may be advantageous for the cavity to open to the outside as such a configuration may make it easier to deposit the product contained in the cavity on surface to be treated.

The cavity/reservoir which opens to the outside further provides air cooling of the product as when the applicator element 6 loaded with the product is removed from the receptacle 2, the product stored in the cavity is exposed to the air from both the sides of the applicator element.

According to the present embodiment, at least one portion of the at least one filament 9 is bent to provide a first loop 13 by giving the at least one portion of the filament 9 a first reverse bend in a direction towards the distal end of the stem 4. A concave side 13a of the first reverse bend of the first loop 13 faces towards the distal end of the stem 4. Further, at least one other portion of the at least one filament 9 is bent again to provide a second loop 14 by giving the at least one other portion of the filament 9, a second reverse bend in a direction towards the distal end of the stem 4. A concave side 14a of the second reverse bend of the second loop 14 faces towards the distal end of the stem 4. According to the present embodiment, the second loop 14 is present inside the first loop 13 or the second loop 14 is at least partially encased by the first loop 13. The first loop 13 is an outer loop and the second loop 14 is an inner loop. Further, according to the present embodiment, the second loop 14 is smaller in dimension as compared to the first loop 13. However, it would not be beyond the ambit of the present disclosure if the second loop 14 is present on top of the first loop 13 such that the first loop 13 and the second loop 14 are substantially similar in dimension.

According to the present embodiment, the first loop 13 includes a pair of legs 15 and 16 and the second loop 14 includes a pair of legs 17 and 18.

According to the present embodiment, the legs 15 and 16 of the first loop 13 lie on opposite sides of the longitudinal axis X of the stem 4 and the legs 17 and 18 of the second loop 14 lie on opposite sides of the longitudinal axis X of the stem 4. According to the present embodiment, the legs 15 and 16 of the first loop 13 and the legs 17 and 18 of the second loop 14 are non parallel to the longitudinal axis X of the stem 4.

According to present embodiment, an end portion of the leg 16 of the first loop 13 is in continuum with a starting portion of the leg 17 of the second loop 14.

Further, according to present embodiment, a third loop 20 is defined by the leg 16 and leg 17, of the first loop 13 and the second loop 14 respectively, which are in continuum. A concave side 20a of the third loop 20 faces away from the distal end of the stem 4.

According to the present embodiment and as shown in FIG. 2c at least two portions 13b, 13c of the first loop 13 lie in two different planes and at least two portions 14b, 14c of the second loop 14 also lie in two different planes.

In alternate embodiments, at least one of the first loop 13 and the second loop 14 may lie in a single plane.

In yet another alternate embodiment, both the first loop 13 and the second loop 14 lie in a single plane.

According to present embodiment, at least a portion 13b of the first loop 13 and at least a portion 14b of the second loop 14 lie in different planes. It would not be beyond the scope of the present disclosure if at least a portion of the first loop 13 and at least a portion of the second loop 14 lie in the same plane.

According to an embodiment, a major portion of one leg from a pair of legs of one loop lies forward of other leg from the pair of legs of said loop.

According to present embodiment and as shown in FIGS. 2a to 2c, the leg 16 of the first loop 13 lies forward of the leg 15 of the first loop 13. Further, the leg 17 of the second loop 14 lies forward of the leg 18 of the second loop 14. Thus, the legs 15 and 16 of the first loop and the legs 17 and 18 of the second loop lie in different planes.

According to present embodiment, a major portion of the first loop 13 lies forward of a major portion of the second loop 14.

Further, according to the present embodiment, the leg 17 of the second loop 14 lies forward of the leg 15 of the first loop 13. Thus, the leg 17 of the second loop 14 and the leg 15 of the first loop 13 lie in different planes.

Further, according to an embodiment, a pair of legs of at least one loop crosses one another at a point but may or may not touch each other at the point of crossing.

According to present embodiment, the legs 17 and 18 of the second loop 14 cross each other at point 19. The leg 17 is referred to as the upper leg and the leg 18 is referred to as the under leg.

The at least one filament 9 is constructed of a material capable of holding and retaining a thermal charge. In other embodiments, the at least one filament 9 is constructed of any suitable material capable of retaining and/or transferring heat or cold during application of the product. For example, the material may include, but is not limited to, metal, glass, and/or ceramics. The metal may include, carbon steel, stainless steel, aluminum, brass, chrome, copper, gold, nickel, platinum, silver, titanium, alloys, combinations thereof, or the like. Further, the material may include a base metal of zinc and alloying elements of aluminum, magnesium, and copper (e.g., Zamac).

In other embodiments, stones, additives, resin, magnetic components, or any other components may be added separately or in combination to the metal, ceramic, and/or glass. For instance, stones may include but are not limited to, jade, opal, turquoise, amethyst, aquamarine, Tiger's eye, coral, amber, quartz, onyx, and tanzanite. In other embodiments, magnetic components may be added that include but are not limited to, magnetic powders, magnetic compounds, or magnetic strips. The magnetic powders may include but are not limited to, ferrite magnetic powder, barium ferrite magnetic powder, strontium ferrite magnetic powder, rare earth magnetic powder, iron oxide compound, a combination of aluminium (aluminum), nickel, and cobalt (Alnico) with iron and small amounts of other components.

Figures 3A, 3B:
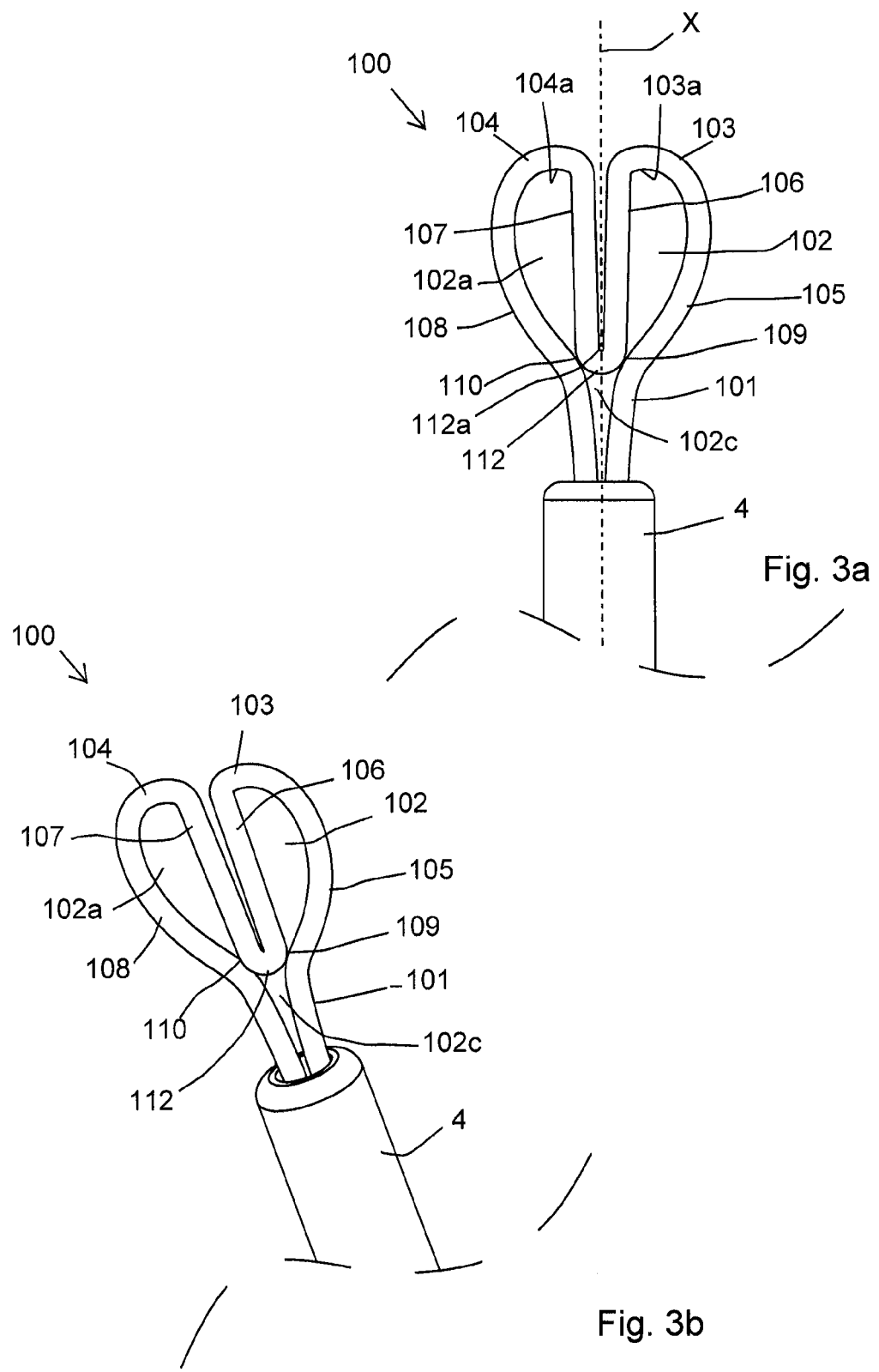
FIG. 3a and FIG. 3b illustrate a front view and a perspective view of an applicator according to second embodiment of the disclosure.

FIGS. 3a and 3b show a front view and a perspective view of an applicator element 100 according to second embodiment of the disclosure.

The applicator element 100 shown in FIGS. 3a and 3b is similar to the applicator element 6 shown in FIGS. 2a to 2c as it also comprises at least one filament 101 similar to the at least one filament 9, made up of a continuous single length of one or more materials, bent to provide a discontinuous application surface by forming at least one cavity/reservoir.

According to present embodiment, the at least one filament 101 is bent to form at least two cavities or reservoirs 102 and 102a for holding the product. The two cavities or reservoirs 102 and 102a are formed by a first loop 103 and a second loop 104 respectively. At least one portion of the at least one filament 101 is bent to form a first loop 103 by giving the at least one portion of the filament 101 a first reverse bend in a direction towards the distal end of the stem 4, such that a leg 105 of the first loop 103 is longer than its leg 106. A concave side 103a of the first reverse bend of the first loop 102 faces towards the distal end of the stem 4. Further, at least one other portion of the at least one filament 101 is bent again to provide an adjacent second loop 104 by giving the at least one other portion of the filament 101 a second reverse bend in a direction towards the distal end of the stem 4, such that a leg 108 of the second loop 104 is longer than its another leg 107. A concave side 104a of the second reverse bend of the second loop 104 faces towards the distal end of the stem 4.

Alternatively, the applicator element may be formed by injection molding, bi-injection molding, multi-injection molding, press molding and the like.

According to the present embodiment, the legs 105 and 106 of the first loop 103 lie on one side of the longitudinal axis X of the stem 4 and the legs 107 and 108 of the second loop 14 lie on other side of the longitudinal axis X of the stem 4.

According to the present embodiment, the leg 105 of the first loop 103 and the leg 108 of the second loop 104 are non-parallel to the longitudinal axis X of the stem 4 whereas the leg 106 of the first loop 103 and the leg 107 of the second loop 14 are parallel to the longitudinal axis X of the stem 4.

According to present embodiment, the first loop 103 and the second loop 104 are adjacent to each other and lie in the same plane.

According to a variant of the second embodiment, the first loop 103 and the second loop 104 may not lie in the same plane.

Further, according to present embodiment, the legs 105 and 106 of the first loop 103 contact each other at a point 109. The legs 107 and 108 of the second loop 104 contact each other at point 110.

Further, according to present embodiment, an end point of the leg 106 contacts the leg 105 at a point 109 and an end point of the leg 107 contacts the leg 108 at a point 110 such that the remaining portion of the legs 105 and 108 form another cavity 102c.

Further, according to present embodiment, end portion of the leg 106 of the first loop 103 is in continuum with starting portion of the leg 107 of the second loop 104.

According to present embodiment, a third loop 112 is defined by the leg 106 of the first loop 103 and the leg 107 of the second loop 104, which are in continuum. A concave side 112a of the third loop 112 faces away from the distal end of the stem 4.

Figure 4A:
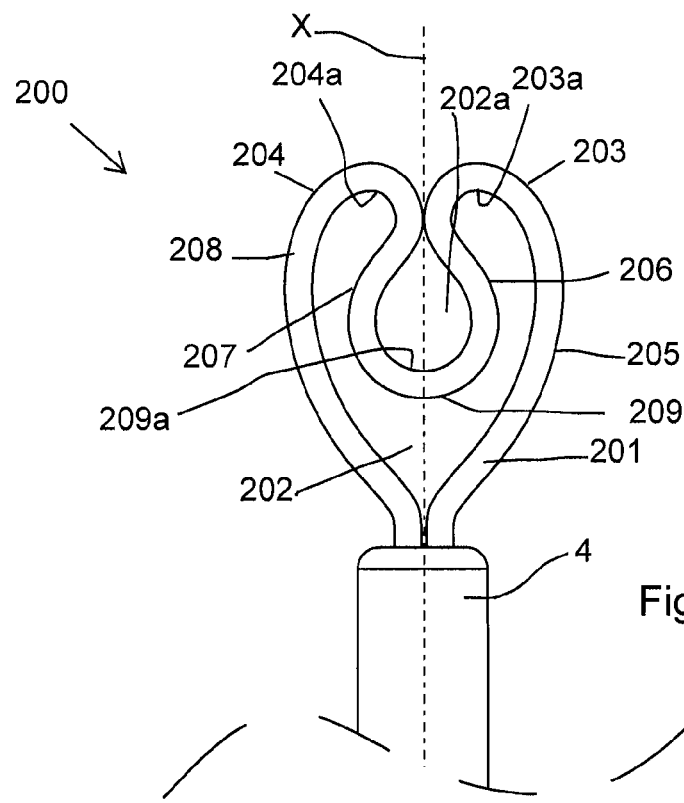
FIG. 4a and FIG. 4b illustrate a front view and a perspective view of an applicator according to third embodiment of the disclosure.
Figure 4B:
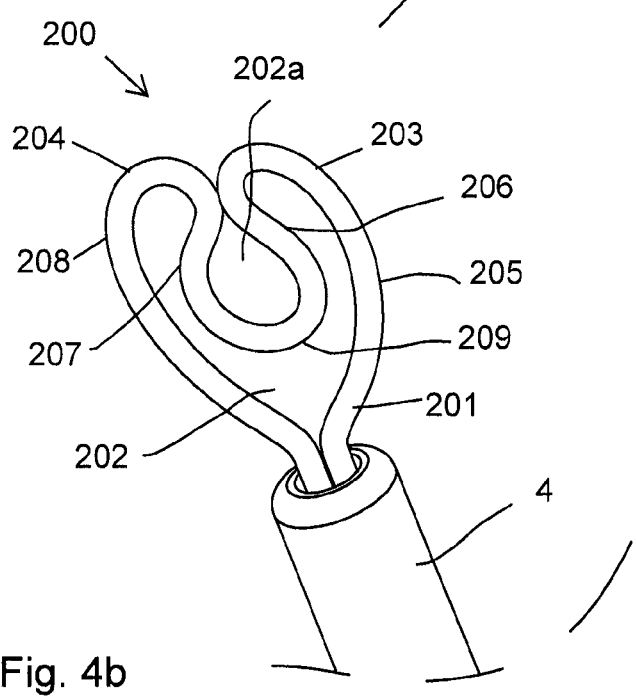

FIGS. 4a and 4b show a front view and a perspective view of an applicator element 200 according to third embodiment of the disclosure.

The applicator element 200 shown in FIGS. 4a and 4b is similar to the applicator element 6 shown in FIGS. 2a to 2c as it also comprises at least one filament 201 similar to the at least one filament 9, bent to provide a discontinuous application surface by forming at least one cavity/reservoir.

According to the present embodiment, the at least one filament 201 is bent to provide at least one cavity/reservoir 202 for holding the product. The at least one cavity/reservoir 202 is formed by two loops 203 and 204. At least one portion of the at least one filament 201 is bent to provide a first loop 203 by giving the at least one portion of the filament 201 a first reverse bend in a direction towards the distal end of the stem 4, such that a leg 205 of the first loop 203 is longer than its leg 206. A concave side 203a of the first reverse bend of the first loop 203 faces towards the distal end of the stem 4. Further, the leg 206 is curved such that it is substantially parallel to the leg 205. Further, at least one other portion of the at least one filament 201 is bent again to provide a second loop 204 by giving the at least one other portion of the filament 201, a second reverse bend in a direction towards the distal end of the stem 4, such that a leg 208 of the loop 204 is longer than its leg 207. A concave side 204a of the second reverse bend of the second loop 204 faces towards the distal end of the stem 4. Further, the leg 207 is curved such that it is substantially parallel to the leg 208.

According to the present embodiment, the legs 205 and 206 of the first loop 203 lie on one side of the longitudinal axis X of the stem 4 and the legs 207 and 208 of the second loop 204 lie on other side of the longitudinal axis X of the stem 4.

According to the present embodiment, the legs 205 and 206 of the first loop 203 and the legs 207 and 208 of the second loop 204 are non parallel to the longitudinal axis X of the stem 4.

Further, according to the present embodiment, the legs 206 and 207 of the respective loops 203 and 204 are in continuum and together form a third loop 209 which further form another cavity/reservoir 202a for holding the product. A concave side 209a of the third loop 209 faces away from the distal end of the stem 4.

According to the present embodiment the first loop 203 and the second loop 204 are separated by the third loop 209 such that the loops 203, 204 and 209 lie in the same plane.

According to a variant of the third embodiment, the loops 203, 204, and 209 may not lie in the same plane.

Figure 5A:
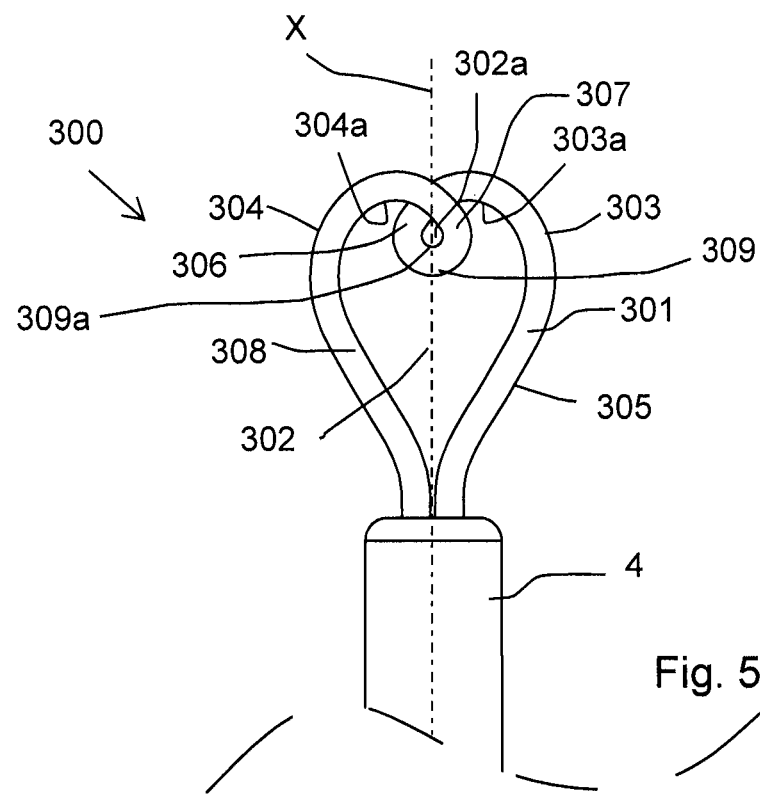
FIG. 5a and FIG. 5b illustrate a front view and a perspective view of an applicator according to fourth embodiment of the disclosure.
Figure 5B:
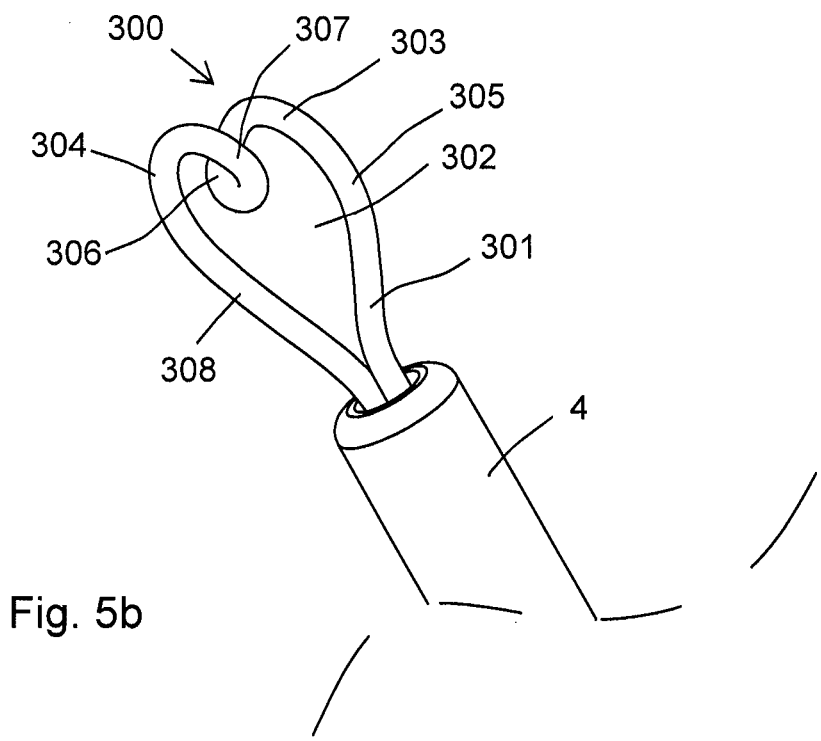

FIGS. 5a and 5b show a front view and a perspective view of an applicator element 300 according to fourth embodiment of the disclosure.

The applicator element 300 shown in FIGS. 5a and 5b is similar to the applicator element 6 shown in FIGS. 2a to 2c as it also comprises at least one filament 301 similar to the at least one filament 9, bent to provide a discontinuous application surface by forming at least one cavity/reservoir.

According to present embodiment, the at least one filament 301 is bent to provide at least one cavity/reservoir 302 for holding the product. The at least one cavity/reservoir 302 is formed by two loops 303 and 304. At least a portion of the at least one filament 301 is bent to provide a first loop 303 by giving the at least one portion of the at least one filament 301 a first reverse bend in a direction towards the distal end of the stem 4, such that the first loop 303 has one leg 305 longer than its another leg 306. A concave side 303a of the first reverse bend of the first loop 303 faces towards the distal end of the stem 4. Further, at least one other portion of the at least one filament 301 is bent again to provide a second loop 304 by giving the at least one other portion of the at least one filament 301 a second reverse bend in a direction towards the distal end of the stem 4, such that the second loop 304 also has one leg 308 longer than its another leg 307. A concave side 304a of the second reverse bend of the second loop 304 faces towards the distal end of the stem 4.

According to the present embodiment, the legs 305 and 306 of the first loop 303 lie on opposite sides of the longitudinal axis X of the stem 4 and the legs 307 and 308 of the second loop 304 lie on opposite sides of the longitudinal axis X of the stem 4.

According to the present embodiment, the legs 305 and 306 of the first loop 303 and the legs 307 and 308 of the second loop 304 are non parallel to the longitudinal axis X of the stem 4.

Further, according to present embodiment, end portion of the leg 306 of the first loop 303 is in continuum with starting portion of the leg 307 of the second loop 304.

According to present embodiment, a third loop 309 forming a cavity 302a is defined by the leg 306 of the first loop 303 and the leg 307 of the second loop 304, which are in continuum. A concave side 309a of the third loop 309 faces away from the distal end of the stem 4.

According to the present embodiment, a portion of the first loop 303 and a portion of the second loop 304 lie in different planes. The leg 306 of the first loop 303 and the leg 307 of the second loop 304 cross each other at a point (not shown) such that the leg 306 is the under leg and the leg 307 is the upper leg.

FIGS. 6a and 6b show a front view and a perspective view of an applicator element 400 according to fifth embodiment of the disclosure.

The applicator element 400 shown in FIGS. 6a and 6b comprises at least one filament 401 similar to the at least one filament 9, bent to provide a discontinuous application surface by forming at least one cavity/reservoir. The at least one filament 401 is a continuous single length of one or more materials.

According to the present embodiment, the at least one filament 401 is bent to provide at least one cavity/reservoir 402 for holding the product. The at least one cavity/reservoir 402 is formed by a first loop 403. At least a portion of the at least one filament 401 is bent to provide a first loop 403 by giving the at least one portion of the filament 401 a first reverse bend in a direction towards the distal end of the stem 4, such that the first loop 403 has a leg 405 longer than its leg 406. A concave side 403a of the first reverse bend faces towards the distal end of the stem 4. Further the leg 405 and the leg 406 lie in different planes such that the leg 406 is upper leg and the leg 405 is under leg and the legs 405 and 406 cross each other at a point 407. Further, at least one other portion of the at least one filament 401 is bent again to provide a second loop or curve 404 by giving the at least one other portion of the filament 401 a second reverse bend in a direction towards the distal end of the stem 4, such that the first loop 403 and the second loop 404 are in close contact or substantially contiguous with each other. A concave side 404a of the second reverse bend faces towards the distal end of the stem 4. Further, the second loop 404 has a leg 408 smaller in length to its leg 409. Further the leg 408 and the leg 409 lie in same plane such that the leg 408 and the leg 409 are at same level and the leg 409 meets the leg 405 at a point 410. Further, at least one other portion of the at least one filament 401 is bent again to provide a third loop 411 by giving the at least one portion of the filament 401 a third reverse bend in a direction towards the distal end of the stem 4 such that the third loop 411 has two legs 412 and 413. At least one portion of each of the legs 412 and 413 lie on one side of the longitudinal axis X of the stem 4 and at least one other portion of each of the legs 412 and 413 lie on opposite side of the longitudinal axis X of the stem 4. In other words, at least one other portion of the at least one filament 401 is bent to provide a third loop 411 by bending the at least one other portion other portion in form of "S" before giving a reverse bend in a direction towards the distal end of the stem 4. Further, the leg 412 is an under leg and the leg 413 is an upper leg and the legs 412 and 413 cross each other at a point (not shown). The third loop 411 forms a second cavity 402a.

According to the present embodiment, the leg 405 of the first loop 403 is parallel to the longitudinal axis X of the stem 4 whereas the leg 406 of the first loop 403, the legs 408 and 409 of the second loop 404 and the legs 412 and 413 of the third loop 411 are non parallel to the longitudinal axis X of the stem 4.

According to an embodiment, the legs 412 and 413 may or may not touch each other at the point of crossing.

It would not be beyond the ambit of the present disclosure if the lower portions of the legs 412 and 413 crossing and touching each other at a point may form another loop.

According to the present embodiment, the first loop 403, the second loop 404 and the third loop 411 lie in different planes.

According to the present embodiment, the first loop 403, the second loop 404 and the third loop 411 lie along the longitudinal axis X of the stem 4.

In alternate embodiments of the present disclosure, as shown in FIGS. 7-12b, the applicator may comprise at least two applicator elements, and wherein one applicator element of the at least two applicator elements comprises at least one filament which is bent to provide a discontinuous application surface by forming at least one cavity/reservoir and at least one loop. Furthermore, the one of the at least two applicator elements at least partially surrounds or encompasses the other of the at least two applicator elements. All of these alternate embodiments will be explained in detail hereinafter.

Figure 7:
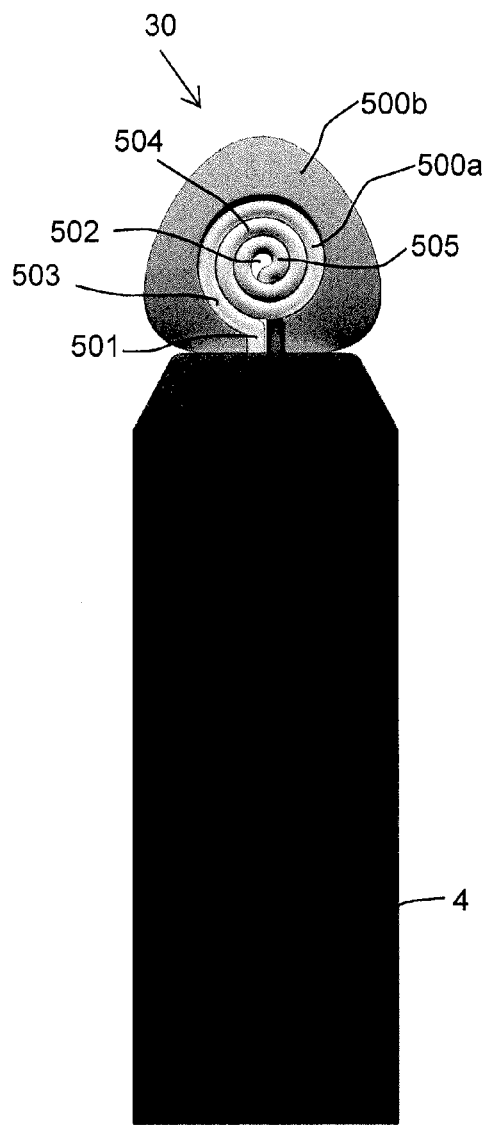
FIG. 7 illustrates a front view of an applicator according to sixth embodiment of the disclosure.

FIG. 7 shows a front view of an applicator 30 according to sixth embodiment of the disclosure. The applicator 30 is similar to applicators 3 of FIGS. 1-6b in aspect that the applicator 30 includes a first applicator element 500a comprising at least one filament 501 bent to provide a discontinuous application surface by forming at least one cavity/reservoir 502 for holding the product. The applicator element 500a comprises at least two loops 503, 504, 505 extending in a direction of the applicator 30. The at least two loops comprising a first loop 503 and a second loop 504. The first loop 503 is formed by giving a first reverse bend to at least one portion of the at least one filament 501, in a direction towards the distal end of the stem 4 such that a concave side of the first reverse bend of the first loop 503 faces towards the distal end of the stem 4. The second loop 504 is formed by giving a second reverse bend to at least one another portion of the at least one filament 501, in a direction towards the distal end of the stem 4 such that a concave side of the second reverse bend of the second loop 504 faces towards the distal end of the stem 4. However it differs in some aspects as explained. The applicator 30 includes a second applicator element 500b which at least partially surrounds or encompasses the first applicator element 500a. The second applicator element 500b may be made up of a material such as metal, plastic, silicone, sponge, foam, alloy, ceramic, stone, wood, rubber, sintered, porous material and/or combinations thereof or other suitable material. In variant embodiments, the second applicator element 500b may be flocked. Further, as seen in FIG. 7, the second applicator element 500b partially surrounds or encompasses the first applicator element 500a in a manner that the cavity 502 is open to outside and such a configuration may make it easier to deposit the product contained in the cavity 502 on a surface to be treated and provides air cooling of the product when the applicator 30 is removed from the receptacle (not shown). Further, the at least one filament 501 is a continuous single length of one or more materials.

Figure 8A:
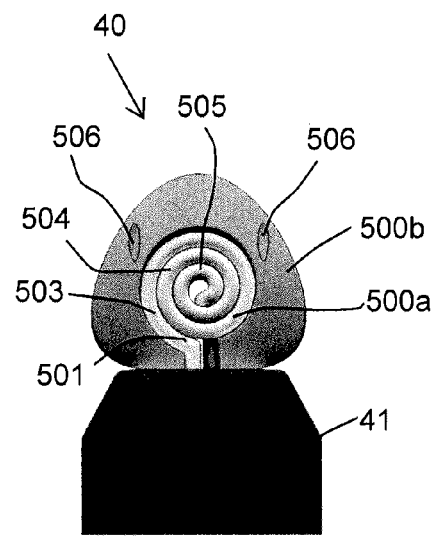
FIG. 8a and FIG. 8b illustrate a front view and a perspective view of an applicator according to seventh embodiment of the disclosure.
Figure 8B:
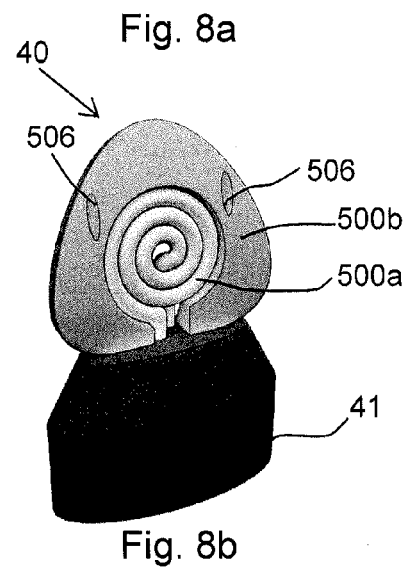

Referring now to FIGS. 8a and 8b, an applicator 40 is provided which is similar to applicator 30 of FIG. 7 except in that the applicator 40 is a flow through applicator 40 and the second applicator element 500b of the applicator 40 includes at least one orifice 506 designed to dispense a cosmetic product onto an application surface of the second applicator element 500b. The first applicator element 500a includes at least one loop 503, 504, 505 formed by reverse bending at least a portion of the at least one filament 501 in a direction towards the proximal end of the applicator 40 or distal end of a collar/holder 41. Further, the connecting collar/holder 41 is provided for securely mounting the applicator 40 to a cosmetic container having a receptacle for holding the cosmetic product (not shown) and wherein the cosmetic product is dispensed from the cosmetic container through the at least one orifice 506 of the second applicator element 500b.

Figure 9:
FIG. 9 illustrates a front view of an applicator according to eighth embodiment of the disclosure.

FIG. 9 shows a front view of an applicator 50 according to eighth embodiment of the disclosure. The applicator 50 is similar to applicator 30 of FIG. 7 except in that a first applicator element 600a at least partially surrounds or encompasses a second applicator element 600b. The first applicator element 600a comprises at least one filament 601 bent to provide a discontinuous application surface by forming at least one cavity (not visible) and wherein the second applicator element 600b is at least partially housed within the cavity. Further, the first applicator element 600a includes at least one loop 603, 604, 605 formed by reverse bending at least a portion of the at least one filament 601 in a direction towards the distal end of the stem 4.

Figure 10A:
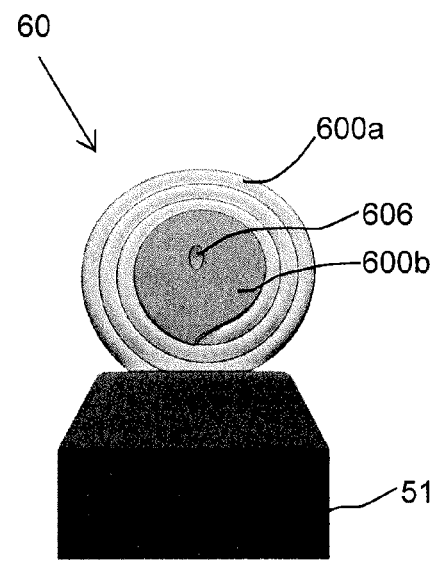
FIG. 10a and FIG. 10b illustrate a front view and a perspective view of an applicator according to ninth embodiment of the disclosure.
Figure 10B:
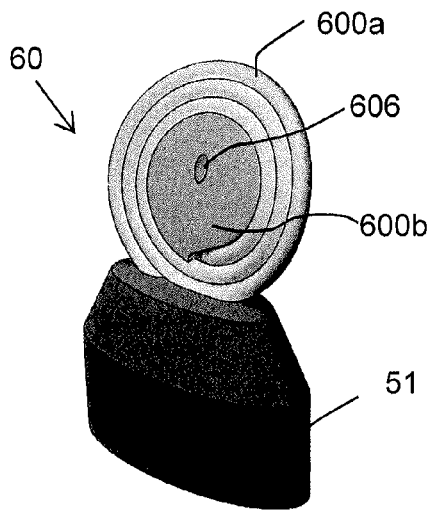

FIGS. 10a and 10b shows a front view and a perspective view of an applicator 60 according to ninth embodiment of the disclosure. The applicator 60 is similar to the applicator 50 of FIG. 9 except in that the applicator 60 is a flow through applicator 60 and wherein the second applicator element 600b of the applicator 60 includes at least one orifice 606 designed to dispense a cosmetic product onto an application surface of the second applicator element 600b. Further, the applicator 60 includes a connecting collar/holder 51 for securely mounting the applicator 60 to a cosmetic container having a receptacle for holding the cosmetic product (not shown) and wherein the cosmetic product is dispensed from the container through at least one orifice 606 of the second applicator element 600b.

Figure 11:
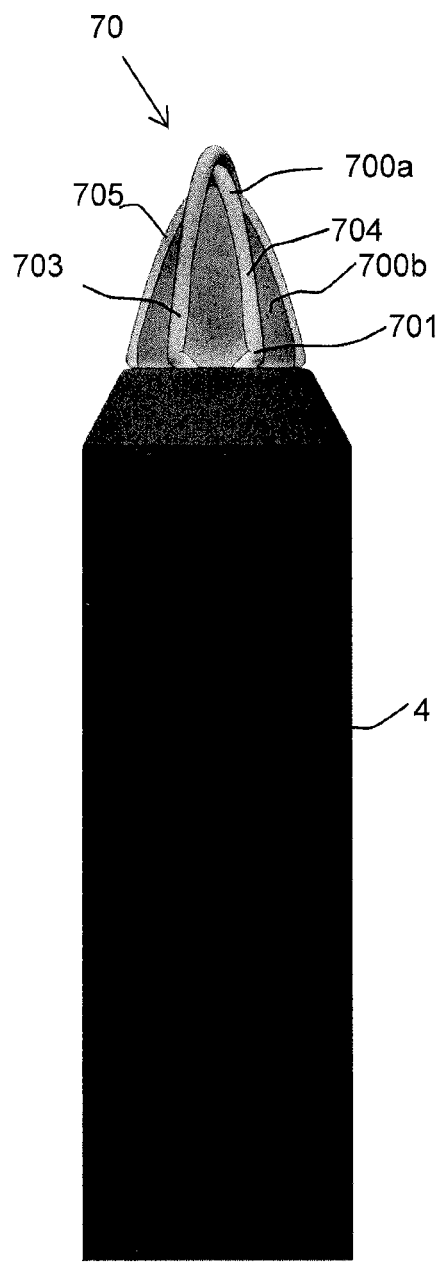
FIG. 11 illustrates a front view of an applicator according to tenth embodiment of the disclosure.

FIG. 11 shows a front view of an applicator 70 according to tenth embodiment of the disclosure. The applicator 70 comprises a first applicator element 700a which at least partially surrounds or encompasses a second applicator element 700b. The first applicator element 700a comprises at least one filament 701 bent to provide a discontinuous application surface by forming at least one cavity (not visible) and wherein the second applicator element 700b is at least partially housed within the cavity. Further, the first applicator element 700a includes at least one loop 703, 704, 705 formed by reverse bending at least a portion of the at least one filament 701 in a direction towards the distal end of the stem such that the at least one loop 703, 704, 705 forms a cage like structure for partially encompassing the second applicator element 700b. The second applicator element 700b is a porous material e.g. sponge, foam or like, desirably shaped to fit within cavity of the first applicator element 700a.

Figure 12A:
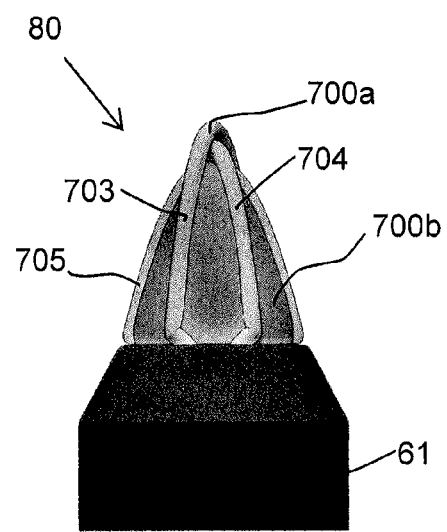
FIG. 12a and FIG. 12b illustrate a front view and a perspective view of an applicator according to eleventh embodiment of the disclosure.
Figure 12B:
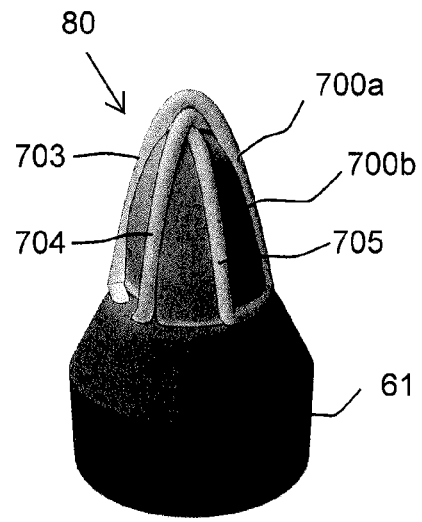

FIGS. 12a and 12b shows a front view and a perspective view of an applicator 80 according to ninth embodiment of the disclosure. The applicator 80 is similar to the applicator 70 of FIG. 11 except in that the applicator 80 is a flow through applicator and wherein the second applicator element 700b of the applicator 80 is designed to dispense a cosmetic product onto an application surface of the second applicator element 700b due to its porosity. The first applicator element 700a includes at least one loop 703, 704, 705 formed by reverse bending at least a portion of the at least one filament 701 in a direction towards the proximal end of the applicator 80 or distal end of a collar/holder 61. The applicator 80 includes a connecting collar/holder 61 for securely mounting the applicator to a cosmetic container having a receptacle for holding the product (not shown) and wherein the product is dispensed from the container through the second applicator element 700b due to its porosity.

In all the embodiments described above different portions of one or more material may be connected or integrally molded together to form loops to provide a discontinuous application surface. The two or more portions may be connected together or formed as one by various attachment means like adhesive, snap fitting, integrally molded, press molding and the like.

In all the embodiments, the at least one filament may have a circular or a non-circular cross-section such as oval, elliptic, or polygonal cross-section.

Although the foregoing is directed to embodiments of the present disclosure, other and further embodiments of the disclosure may be devised without departing from the basic scope thereof, and the scope thereof is determined by the claims that follow. Accordingly, the appended claims should be construed to encompass not only those forms and embodiments of the disclosure specifically described above, but to such other forms and embodiments as may be devised by those skilled in the art without departing from its true spirit and scope.

What is claimed is:

1. An applicator comprising:
a stem having a proximal end and a distal end;
at least two applicator elements at the distal end of the stem;
wherein one of the at least two applicator elements comprises at least one filament, the at least one filament is at least partially constructed from a thermal storage material;
wherein at least one end of the at least one filament is attached to the distal end of the stem;
wherein the at least one applicator element comprises at least two loops extending in a direction of the applicator;
wherein the at least two loops comprising a first loop and a second loop;
wherein the first loop is formed by giving a first reverse bend to at least one portion of the at least one filament, in a direction towards the distal end of the stem such that a concave side of the first reverse bend of the first loop faces towards the distal end of the stem;
wherein the second loop is formed by giving a second reverse bend to at least one another portion of the at least one filament, in a direction towards the distal end of the stem such that a concave side of the second reverse bend of the second loop faces towards the distal end of the stem; and
wherein one of the at least two applicator elements at least partially surrounds other of the at least two applicator elements.

2. An applicator according to claim 1, wherein the thermal storage material is selected from a group of metal, alloy, glass, stone, resin and ceramics.

3. An applicator according to claim 1, wherein the first loop and the second loop form one or more cavities.

4. An applicator according to claim 1, wherein the second loop is partially encased by the first loop.

5. An applicator according to claim 1, wherein, other of the at least two applicator elements is made up of a material selected from a group consisting of metal, plastic, silicone, sponge, foam, alloy, ceramic, stone, wood, rubber, sintered, porous material and/or combinations thereof.

6. An applicator according to claim 1, wherein each of the at least two loops has a pair of legs and wherein the first loop comprises a first pair of legs including a first leg and a second leg and the second loop comprises another pair of legs including a first leg and a second leg.

7. An applicator according to claim 6, wherein the first leg and the second leg of at least the first loop or the second loop lie on opposite sides of a longitudinal axis of the stem.

8. An applicator according to claim 6, wherein the first leg and the second leg of at least the first loop or the second loop are non-parallel to a longitudinal axis of the stem.

9. An applicator according to claim 6, wherein a third loop is defined by the second leg of the first loop and the first leg of the second loop which are in continuum, and wherein a concave side of the third loop faces away from the distal end of the stem.

10. An applicator according to claim 6, wherein the first leg and the second leg of at least the first loop or the second loop lie on same side of a longitudinal axis of the stem.

11. An applicator according to claim 6, wherein the pair of legs of at least one of the at least two loops crosses one another at a point.

12. An applicator according to claim 1, wherein different portions of the at least one filament are constructed from different materials and wherein the different portions are connected together by an attachment means selected from adhesive, snap fitting, integrally molded and press molding.

13. An applicator according to claim 1, wherein the at least two loops of the at least one applicator element form a cage like structure which partially encompasses the other of the at least two applicator elements.

14. A flow-through applicator comprising:
at least two applicator elements;
wherein one of the at least two applicator elements comprises at least one filament, the at least one filament is at least partially constructed from a thermal storage material;
wherein the one of the at least two applicator elements comprises at least two loops extending in a direction of the flow-through applicator;

wherein the at least two loops comprising a first loop and a second loop;

wherein the first loop is formed by giving a first reverse bend to at least one portion of the at least one filament, in a direction towards a proximal end of the flow-through applicator such that a concave side of the first reverse bend of the first loop faces towards the proximal end of the flow-through applicator;

wherein the second loop is formed by giving a second reverse bend to at least one another portion of the at least one filament, in a direction towards the proximal end of the flow-through applicator such that a concave side of the second reverse bend of the second loop faces towards the proximal end of the flow-through applicator; and wherein other of the at least two applicator elements includes at least one dispensing orifice designed to dispense a cosmetic product onto an application surface of the other applicator element.

15. A flow-through applicator according to claim 14, wherein the at least two loops of the one of the at least two applicator elements form a cage like structure which partially encompasses the other of the at least two applicator elements.

16. A flow-through applicator according to claim 14, wherein one of the at least two applicator elements at least partially surrounds other of the at least two applicator elements.

17. A flow-through applicator according to claim 14, wherein the other of the at least two applicator elements is made up of a material selected from a group consisting of metal, plastic, silicone, sponge, foam, alloy, ceramic, stone, wood, rubber, sintered, porous material and/or combinations thereof.

18. A flow-through applicator according to claim 14, wherein the flow-through applicator includes a connecting collar for securely mounting the flow-through applicator to a cosmetic container having a receptacle for holding the cosmetic product.

19. A flow-through applicator according to claim 14, wherein the thermal storage material is selected from a group of metal, alloy, glass, stone, resin and ceramics.

20. A flow-through applicator comprising:
at least one applicator element;
wherein the at least one applicator element comprises at least one filament, the at least one filament is at least partially constructed from a thermal storage material;
wherein the at least one applicator element comprises at least two loops extending in a direction of the flow-through applicator;
wherein the at least two loops comprising a first loop and a second loop;
wherein the first loop is formed by giving a first reverse bend to at least one portion of the at least one filament, in a direction towards a proximal end of the flow-through applicator such that a concave side of the first reverse bend of the first loop faces towards the proximal end of the flow-through applicator; and
wherein the second loop is formed by giving a second reverse bend to at least one another portion of the at least one filament, in a direction towards the proximal end of the flow-through applicator such that a concave side of the second reverse bend of the second loop faces towards the proximal end of the flow-through applicator.

* * * * *